US00PP19178P3

(12) United States Plant Patent

Maillard et al.

(10) Patent No.: US PP19,178 P3

(45) Date of Patent: Sep. 2, 2008

(54) PEACH TREE NAMED 'CRISPREGAL'

(50) Latin Name: ***Prunus persica* var. *nucipersica***
Varietal Denomination: Crispregal

(75) Inventors: Arsene Maillard, Elne (FR); Laurence Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 0 days.

(21) Appl. No.: 11/783,784

(22) Filed: Apr. 12, 2007

(65) Prior Publication Data

US 2007/0250973 P1 Oct. 25, 2007

(30) Foreign Application Priority Data

Apr. 24, 2006 (FR) ..... 2006-0997

(51) Int. Cl.
*A01H 5/00* (2006.01)

(52) U.S. Cl. ..... Plt./197

(58) Field of Classification Search ..... Plt./197
See application file for complete search history.

*Primary Examiner*—Anne Marie Grunberg
*Assistant Examiner*—Louanne C Krawczewicz Myers
(74) *Attorney, Agent, or Firm*—Westerman, Hattori, Daniels & Adrian, LLP.

(57) ABSTRACT

A new and distinct variety of peach tree, denominated 'Crispregal', has fruit of very long shelf life without alteration after harvesting, a semi-sweet yellow flesh of high eating quality and an attractive, very high percentage red skin. The tree is of large size and is vigorous. Moreover fruit can be consumed crunchy or melting.

4 Drawing Sheets

This application claims priority of Community plant variety right No. 2006/0997 filed on Apr. 24, 2006 which is hereby incorporated by reference in its entirety.

Latin name of the genus and species of the plant claimed: *Prunus persica* var. *nucipersica.*

Variety denomination: 'Crispregal'.

BACKGROUND OF THE NEW VARIETY

The present invention relates to a new and distinct variety of peach tree, *Prunus persica* var. nucipersica, which has been given the variety denomination 'Crispregal'. This new tree produces fruit with a long shelf life without alteration both on the tree after growth completion and after harvesting, very good eating quality, clingstone flesh fruit for fresh market in end of July to beginning of August in the Pyrénées-Orientales departement, France. Contrast is made to 'Mercil' (O'Henry) U.S. Plant Pat. No. 2,964 to Grant Merrill (as indicated in U.S. Plant Pat. No. PP4,508). 'Merdame' (Elegant Lady®) (U.S. Plant Pat. No. 4,399) peaches, standard varieties, for reliable description. 'Crispregal' is a promising candidate for commercial success in that it has fruit with very long shelf life without alteration after harvesting, and so a very durable fruit.

ORIGIN OF THE VARIETY

'Crispregal' peach tree originated in a cultivated area of the south of France, in the Pyénées-Orientales departement where it was tested. The 'Crispregal' variety results from a pollinated cross of an unnamed yellow peach tree was used as the seed parent. The unnamed yellow peach tree was originated by using 'Julie' while peach tree as seed parent and 'Zaitabo' (Big Top®) yellow nectarine tree as pollen parent. Pollen parent of 'Crispregal' variety is an unnamed yellow nectarine tree, issued from a free pollination of 'Zaitabo' (Big Top®) variety, which was used as seed parent. 'Crispregal' was provisionally designated, tested and genetically identified by a genetic profile, as 03.05.139 PJ - ASF 0441 and is registered at the Official Catalogue of the Agriculture Ministry of the French Republic Dec. 27, 2005 under number 1018860. It was obtained by hybridizing and propagated by grafting. It has been determined to have unique tree and fruit characteristics making it worthy for commercial fresh fruit production. There are not known effects of this standard rootstock on this scion cultivar. Asexually propagated plants remained true to the original tree and all characteristics of the tree and the fruit were transmitted. The plant was reproduced asexually by us in Elne, Pyrénées-Orientales departement, France.

SUMMARY OF THE VARIETY

The new and distinct variety of peach tree blooms in March at Perpignan in the Pyrénées-Orientales departement, France. More particularly, it blooms between $13^{th}$ and $23^{th}$ of March, at the same time than 'Mercil' (O'Henry®), four days after 'Merdame' (Elegant Lady®) (U.S. Plant Pat. No. 4,399) variety.

The first fruit of 'Crispregal' peach tree ripens in July, 3 days before the first fruit of 'Merdame' (Elegant Lady®) (U.S. Plant Pat. No. 4,399) variety. More particularly, it approximately ripens between July $23^{th}$ and August $1^{st}$. The date of maturity varies slightly with the prevailing climatic conditions. More particularly, the date of maturity varies by 5 or 6 days, which can be due to climatic conditions during a 2-months period before blooming.

DESCRIPTION OF THE DRAWINGS

In the accompanying drawing, which are as nearly true as it is reasonably possible to make in a color illustration of this type.

Figure 1:
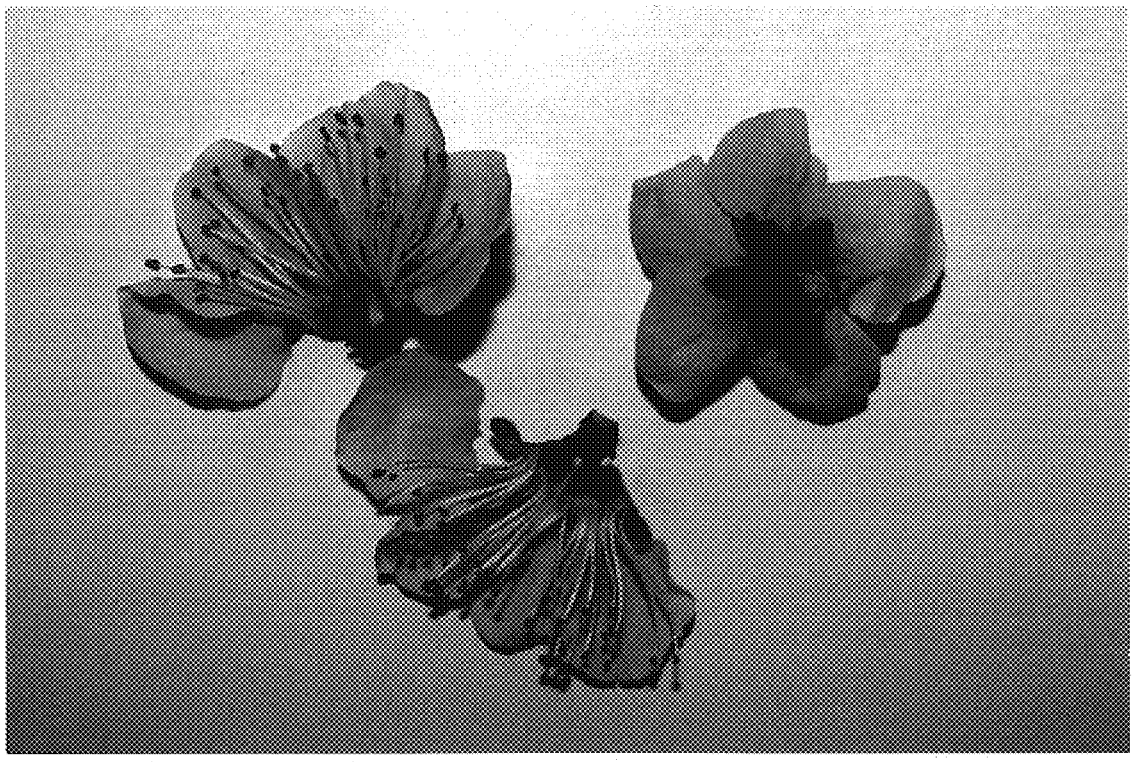
FIG. 1 is a color photograph which depicts the reverse and side view of the flower and the reproductive organs with petals removed of the new variety.
Figure 2:
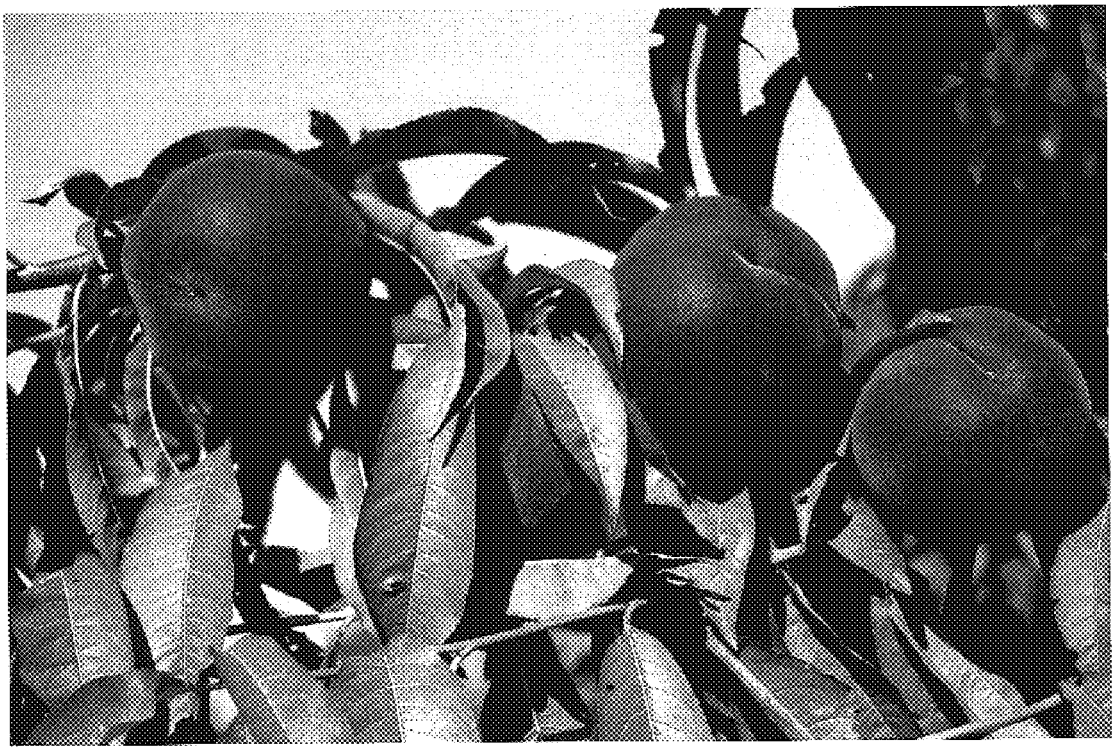
FIG. 2 is a color photograph which shows typical specimens of the fruit on the tree, the leaf and branch of the new variety.
Figure 3:
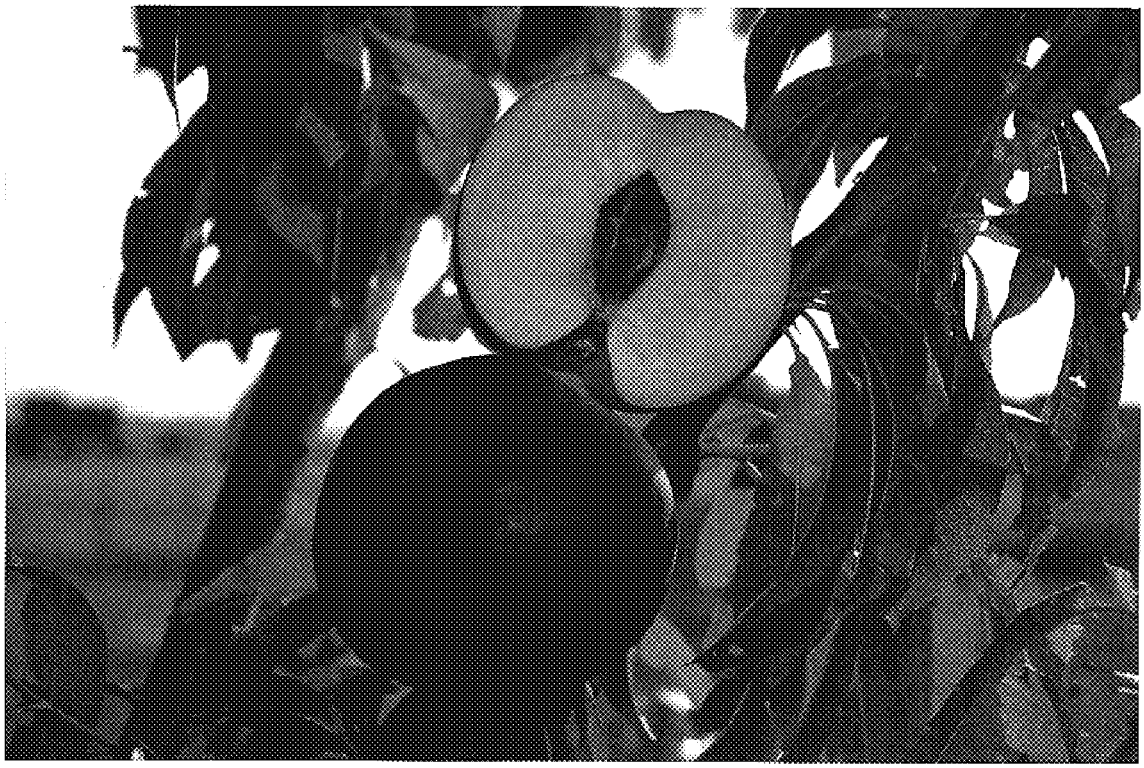
FIG. 3 is a color photograph which shows typical specimens of the fruit on the tree, the leaf and branch of the new variety, and a half part of a fruit which has been cut in half with the pit being left in the presented half part for depicting fruit flesh and stone of the new variety.
Figure 4:
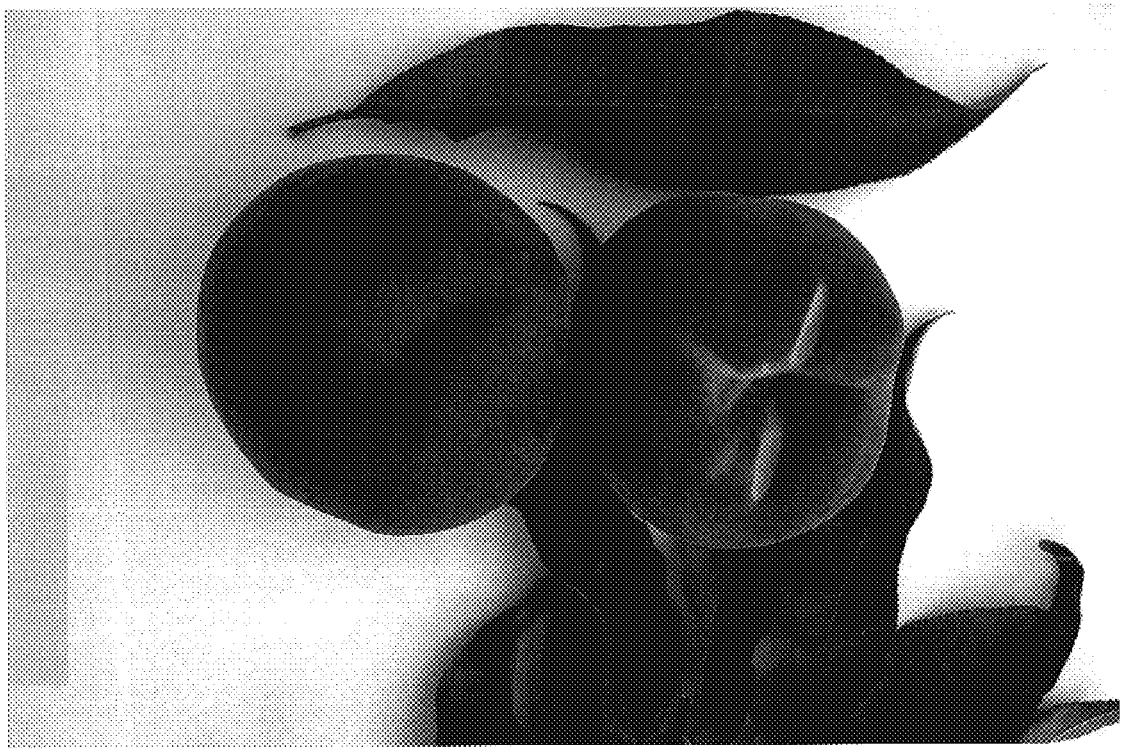
FIG. 4 is a color photograph which shows two whole fruit sufficiently mature for harvesting and shipment and a dorsal view of a single leaf.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic conditions. The potential for commercial production of fresh fruit by 'Crispregal' is high, due to fruit very long shelf life without alteration after harvesting.

Trees are vigorous and large stature half-standing in a semi-spread to semi-upright out aspect. The flowering shoot is present excluding brushwood side away from sun. Flowering begins semi-late in springtime. The type of flower is showy with relative medium petal size. Petals are pink. Leaf glands are present and reniform. Time of maturity for consumption is medium. The fruit flesh is yellow and its skin is very thick, of red blush color with a yellow-orange background. The stone is medium size and the flesh is adherent to the stone. Fruit taste is semi-sweet.

Compared to 'Merdame' (Elegant Lady®) (U.S. Plant Pat. No. 4,399) variety, 'Crispregal' has the same time of maturity with a difference of 3 days, although the red fruit coloration is brighter than for 'Merdame' (Elegant Lady®) (U.S. Plant Pat. No. 4,399) variety. The round shape of the fruit is also more homogeneous. 'Crispregal' variety is clingstone, although 'Merdame' (Elegant Lady®) (U.S. Plant Pat. No. 4,399) variety has a free stone. Shelf life of 'Crispregal' fruit is very long instead of being short, both on the tree and after harvesting. Fruit of 'Crispregal' variety has a better appearance, a slower maturation and a sweeter taste. Moreover fruit can be consumed crunchy or melting.

In summary, compared to 'Zaitabo' (Big Top), 'Crispregal' is a yellow peach, whereas 'Zaitabo' is a yellow nectarine, although 'Crispregal' fruit has similar sweet taste and slow maturation as 'Zaitabo'.

In summary, compared to 'Merdame' (Elegant Lady), 'Crispregal' has showy flowers, clingstone fruit with semi-sweet taste and slow maturation, whereas 'Merdame' has non-showy flowers, freestone fruit with balanced taste and standard maturation. In summary, compared to 'Mercil' (O'Henry) variety, 'Crispregal' has earlier maturity by approximately three weeks, 'Crispregal' fruit is clingstone instead of having a free stone, has a round shape instead of a triangular one, as well as a sweeter taste and a slower maturation.

DETAILED DESCRIPTION

Referring more specifically to the pomological details of this new and distinct variety of peach tree, the following has been observed during the fourth fruiting season, corresponding to the fifth growing season, under the ecological conditions prevailing at the orchards located near the town of Elne, Pyrénées-Orientales departement, France. All observations have been done on rootstock cultivar. The rootstock was a 'Franc Inra Montclar®' tree. All major color code designations are by reference to The R.H.S. Color Chart (Fourth Edition) provided by The Royal Horticultural Society of Great Britain.

TREE

Size:

*Generally.*—Considered large as compared to other common commercial peach cultivars. The tree size the first year was approximately 280 cm. The tree was pruned during each following dormant season to a height of approximately 250 cm. Current seasons shoots growth could reach 80 cm. So the tree size from the second year (second and next years) reached a final height of 330 cm with current seasons shots length comprised.

Spread: Approximately 1.0 meter. The whole orchard was oriented to a central leader organisation, with tree lines spaced of 4.0 meters and trees spaced of 1 meter in a same tree line.

Vigor: Considered vigorous. The present variety grew from about 200 cm to 280 cm in height during the first growing season. For second and following seasons, the variety was pruned to an approximate height of 250 cm.

Productivity: Very Productive. Fruit set is spaced by thinning to develop the remaining fruit into the desired market sized fruit. The number of the fruit set varies with the prevailing climatic conditions and cultural practices employed during the bloom period, and is therefore not distinctive of the present variety.

Bearer: Very regular. A thinning of 1 fruits on 4 was necessary for the tree valorisation. Thinning may not be too important because of the high magnifying potential of the fruit. Thinning was necessary every year during the past 4 years.

Form: The 'Crispregal' variety has naturally a semi-spread to semi-upright shape.

Density: Considered medium device.

Hardiness: The present tree was grown and evaluated in France. The variety appears to be hardy under typical central Pyrénées-Orientales departement climatic conditions and was selected because of its hardiness. Experimentations on different sites with winter chilling requirement comprised between 350 hours and 1200 hours showed a good behaviour of the tree in all cases. No damages were caused by ascertained temperatures as low as −12 degrees Celsius. The tree was also very resistant to frosty springtime weather.

TRUNK

Diameter: Approximately between 7.0 cm and 8.0 cm in diameter when measured at a distance of approximately 30 cm above the soil level, on trees of the fifth growing season. The branching begins at 50 cm above the soil level.

Bark texture: Considered rough, with numerous folds of papery scarfskin being present.

Lenticels: Numerous lenticels are present on trees of the fifth growing season. The lenticels range in size from approximately 5.0 millimeters to 7.0 millimeters in width, and from 2.0 millimeters to 3.0 millimeters in height.

Lenticel color: The outside of lenticels has a silver-grey color (RHS Grey 201 D to RHS Black 202 D), whereas the inside is considered brown (RHS Greyed Orange 166B).

Bark coloration: The bark has a silver-grey color a little more pronounced than lenticels outside color (RHS Grey 201 C to RHS Black 202 C).

BRANCHES

Size: Mature branches and current season shoots are considered medium to thick for the variety.

Diameter: Average as compared to other peach varieties. The current season shoots have a diameter from 4.0 to 7.0 millimeters, and branches of trees of the fifth growing season have a diameter comprised between 20.0 and 25.0 millimeters.

Surface texture: Average, wood which is several years old has no furrowed appearance.

Crotch angles: Primary branches are considered variable, but the crotch angles are generally between 50 degrees and 70 degrees from the horizontal axis. This particular characteristic is not considered distinctive of the variety, however.

Current season shoots:

*Surface texture.*—Substantially glabrous.

Internode length: Generally 25.0 millimeters to 35.0 millimeters.

Color of mature branches: Medium brown (RHS Grey Brown 199 A).

Current seasons shoots:

*Color.*—The color of new shoot tips is considered a light yellow-green (RHS Yellow Green 144A-B) on lower part of new shoot tips, whereas the upper part is colored in more or less brown-orange (RHS Greyed Orange 173 B-C-D) following the position on the shoot.

LEAVES

Size: Considered medium for the species. Leaf measurements have been taken from vigorous, upright, current-season growth at approximately mid-shoot. The ratio leaf length/leaf width is above 4.

Leaf length: Approximately 160.0 to 195.0 millimeters with leaf petiole.

Leaf width: Approximately 45.0 to 55.0 millimeters.

Leaf base shape: Slightly oblique relative to the leaf longitudinal axis.

Leaf form: Lanceolate.

Leaf tip form: Acuminate.

Leaf color:

*Upper leaf surface.*—Dark Green (RHS Green 137 A).

*Lower surface.*—Medium Green (RHS Green 137 B to 137 C).

Leaf texture: Smooth and glabrous.

Leaf venation: Pinnately veined.

Mid-vein:

*Color.*—Light green with a yellow touch (RHS Yellow Green 144 D to 144 C).

Leaf margins: Slightly undulating.

Form: Considered slightly dentate.

Uniformity: Leaves are isolated or grouped by 2 or 3. In this case, it is found one leaf of normal size with one or two smaller leaves (size-reduction of 50% and more).

Leaf petioles:

*Size.*—Considered medium.

*Length.*—Approximately 12.0 mm.

*Diameter.*—Approximately between 1.8 to 2.3 mm.

*Colour.*—Light green with a yellow touch (RHS Yellow Green 144 D to 144 C).

Leaf glands:

*Size.*—Considered medium.

*Number.*—Generally 3 to 4 glands per leaf.

*Type.*—Reniform.

*Color.*—On young leaves, leaf glands color is considered a pale green (RHS Yellow-Green 144B). On older leaves, leaf glands color turn to a dark brown (RHS Grey Brown 199 A to 199 B).

Leaf stipules:

*Generally.*—No leaf stipules were observed. But as seen in the characteristic relative to the leaves uniformity, it is possible to find leaves by groups of 2 or 3, with a normal-size leaf and smaller ones.

FLOWERS

Flower buds:

*Generally.*—At pre-floral stage of development, the floral buds are conic in form with a round tip. Their form is evolving until blooming, with variable dimensions. Just before blooming, floral buds are approximately 10.0 millimeters wide and approximately 18.0 millimeters long.

Flower buds:

*Color.*—This characteristic is dependent upon the proximity to bloom. At pre-floral stage of development, the bottom of the flowers buds, formed by sepals, is of purple-brown color (RHS Greyed Purple 183 A); the corolla, formed by petals, is generally of pale pink color (RHS Red Purple 69 C). Petals color shows an evolution until the end of flowering. The buds are considered hardy under typical central Pyrénées-Orientales departement climatic conditions.

Hardiness: No winter injury was noted during the last several years of evaluation in the central Pyrénées)Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: Generally March. The first bloom was observed on Mar. 13, 2006.

Blooming time: Considered semi-late season in relative comparison to other commercial peach cultivars grown in the Pyrénées-Orientales departement, France. The date of full bloom is observed on March. The date of bloom varies slightly with climatic conditions and cultural practices. Thus the first full bloom was observed approximately on Mar. 17, 2006.

Duration of bloom: Approximately 11 days. This characteristic varies slightly with the prevailing climatic conditions.

Flower type: The variety is considered to have a showy type flower.

Flower size: Considered medium. Flower diameter at full bloom is approximately 31.0 to 36.0 millimeters.
Bloom quantity: Considered abundant, approximately 25 flowers per meter.
Flower bud frequency; Generally 2 flower buds appear per node, occasionally 1.
Petal size:
*Generally.*—Considered small to medium for the species.
Length: Generally about 17.0 millimeters.
Width: Generally about 16.0 millimeters.
Petal form: Rounded-shaped.
Petal count: Nearly always 5.
Petal texture: Smooth and glabrous.
Petal color: Pink (RHS Red Purple 69 A) when young, slightly darkening with advancing senescence.
Fragrance: Slight.
Petal claw:
*Form.*—The claw is considered to have a conic form with a slightly rounded extremity.
*Length.*—Approximately 8.0 to 10.0 millimeters.
*Width.*—Approximately 6.0 to 8.0 millimeters.
Petal margins: Generally very slightly undulated.
Petal apex:
*Generally.*—The petal apices are generally entire at the tip, and dome-shaped.
Flower pedicel:
*Length.*—Considered medium and having an average length of approximately 3.0 to 5.0 millimeters.
*Diameter.*—Considered average, approximately 2.0 millimeters.
*Color.*—A medium brown (RHS Grey Brown N199 B to C).
Floral nectaries:
*Color.*—A flat gold-orange (Approximately RHS Greyed Red 178 C to B).
Calyx:
*Internal surface texture.*—Smooth and glabrous.
*Color.*—The outer surface of the calyx is considered of Purple-brown (RHS Greyed Purple 183 A) color.
Sepals:
*Surface texture.*—The outer surface has a short, fine pubescent texture.
*Size.*—Average.
*Color.*—Oyroke-brown (RHS Greyed Purple 183A).
Average number of stamens per flower: Approximately 40 stamens per flower.
Anthers:
*Generally.*—Average in length.
*Color.*—Red to orange-red (approximately RHS Greyed Red 178A Group). Anthers are becoming yellow at maturity.
Pollen production: Pollen is abundant, and has a yellow color (Approximately RHS Yellow Orange 17 B-C) changing with maturity. The present variety is considered self fruitful (self-pollinating).
Filaments:
*Size.*—Variable in length, approximately 11.0 to 16.0 millimeters in length. In all cases filament's length is superior to pistil's length. Filaments are shorter than petals.
Color: Considered light pink (approximately RHS Red Purple 62 C-D) to pink (RHS Red Purple 73 A-B).
Pistil:
*Number.*—Generally 1.
*Generally.*—Average in size.
*Length.*—Approximately 15.0 to 21.0 millimeters including the ovary; Smaller than filament's length.
*Color.*—Considered a very pale green (varying from RHS Yellow Green 150 D Group to RHS Yellow Green 151 D Group).
*Surface texture.*—Pubescent at ovary level.

FRUIT

Maturity when described: Firm ripe condition (shipping ripe).
Date of first picking: Jul. 23, 2006.
Date of last picking: Aug. 1, 2006. The date of harvest varies slightly with the prevailing climatic conditions. The 'Crispregal' variety has a medium date of picking, and a grouped maturity: only 2 harvests in 10 days were necessary.
Size:
*Generally.*—Considered vary large, with a homogeneous size between them.
Average cheek diameter: Approximately between 77.0 and 80.0 millimeters.
Average axial diameter: Approximately between 68.0 and 75.0 millimeters.
Typical weight: Generally approximately between 230.0 and 280.0 grams. This characteristic is high dependent upon the prevailing cultural practices, and therefore is not particularly distinctive of the variety.
Fruit form:
*Generally.*—Round to slightly ovate. The fruit is generally uniform in symmetry, view from pistil end.
Fruit suture: Wide-mouthed and smooth, extending from the base to the apex. No apparent callousing or stitching exists along the surface line.
Suture:
*Color.*—This has generally a color similar to the whole fruit color, a red blush (RHS Orange Red N34A) on a yellow-orange background (RHS Yellow Orange 17A).
Ventral surface:
*Form.*—Smooth.
Apex: Non prominent, slightly depressed, very small.
Base: Slightly wide-mouthed, shallow.
Stem cavity: Generally elongated in the suture plane. Average depth of the stem cavity is about 0.7 cm. Average width is about 1.5 cm.
Fruit skin:
*Thickness.*—Considered very thick and strong, and tenacious to moderately tenacious to the flesh depending on stage of maturity.
*Texture.*—Slightly pubescent.
*Taste.*—Semi-sweet.
*Tendency to crack.*—None observed.
Color:
*Blush color.*—This blush color is an homogeneous red (RHS Orange Red N34A). The red blush covers 80% and 90% of the fruit skin surface. The percentage of the blush on the fruit skin surface can vary, and is generally dependent upon the prevailing conditions under which the fruit was grown.
*Ground color.*—The ground color appears on up to 20% of the fruit skin surface, and is considered a yellow-orange (RHS Yellow Orange 17A).
Fruit stem: Medium in length, approximately 7.0 millimeters.
Diameter: Approximately 4.0 millimeters.
Color: Pale green (RHS Yellow Green 145A to 145 B).

Flesh:

*Ripens.*—Very evenly, homogeneous, slow.

*Texture.*—Very firm, very dense, juicy at harvest maturity stage.

*Fibers.*—Not fibrous.

*Aroma.*—Pronounced.

*Eating quality.*—Considered very good and spicy.

*Flavor.*—Considered semi-sweet. The Brix is superior to 13 and acidity comprised between 6 and 9 meq/100 ml. The flavor is considered spicy.

*Juice.*—Very juicy at complete maturity.

*Brix.*—Generally superior to 13.0 degrees. This characteristic varies slightly with the number of fruit per tree; prevailing cultural practices; and the surrounding climatic conditions.

*Flesh color.*—Yellow flesh (RHS Yellow Orange 16B), with slightly red pigmentation (RHS Red 45 A to B) around the stone.

STONE

Type: Clingstone.

Size: Considered medium for the variety. The stone size varies significantly depending upon the tree vigor, crop load and prevailing growing conditions.

Length: Approximately between 34.0 and 38.0 millimeters.

Width: Approximately between 26.0 and 28.0 millimeters.

Diameter: Approximately between 18.0 and 20.0 millimeters.

Form: Elliptic.

Base: Straight.

Apex:

*Shape.*—The stone apex is short, with a small prominent tip.

Stone cavity: Considered medium size, with an elliptic-form and dimensions corresponding to the stone's dimensions.

Stone surface:

*Surface texture.*—The pit is transversely furrowed on its entire surface. Furrows are more pronounced toward the apex. The stone is pitted toward the base. Relief is generally prominent and present basally.

*Ridges.*—The surface texture is generally characterized by more prominent ridges along the ventral edges and is more prominent at the apical tip.

Ventral edge:

*Width.*—Considered small to medium, and having a dimension of approximately 2.0 millimeters at mid-suture.

Dorsal edge:

*Shape.*—Grooved.

Stone color: The color of the dry stone is generally considered a light orange-brown (RHS Greyed Orange 176 D) and occasionally can present until a red-brown coloration (RHS Greyed Red 178B).

Tendency to split: Splitting is absent or very low, depending on climatic conditions between blooming period and stone hardening.

Kernel:

*Size.*—The kernel is considered medium.

*Length.*—Approximately 20.0 millimeters.

*Width.*—Approximately 12.0 millimeters.

*Thickness.*—Approximately 3.0 to 4.0 millimeters.

*Form.*—Considered oblate and elliptic.

*Pellicle.*—Pubescent.

*Color.*—The kernel skin is a light orange-brown (RHS Greyed Orange 167 C) with darker streaks (RHS Greyed Orange 166 C). The almond is cream-white (RHS Orange White 159 D). The kernel and its embryo are mature at the time of fruit maturity.

Use: The subject variety 'Crispregal' is considered to be a peach tree of the medium season of maturity, and which produces fruits that are considered firm, attractively colored. Fruits have a semi-sweet taste and are excellent for uncooked consumption, crunchy or melting when at full maturity. Due to the their flesh quality, firmness and density, they can also be commercialized as $4^{th}$ range product (packed fruit or fruit in bags for example). And they are also useful for both local and very long distance shipping.

Keeping quality: Excellent. Fruit stayed a little more than one week on tree before harvest and then, has stored well more than 4 weeks after harvest at 2.0 degree Celsius. They have a slow maturation and a long shelf life both on the tree after growth completion and after harvesting without alteration.

Shipping quality: Considered very good. The fruit of the new peach variety showed minimal bruising of the flesh or skin damage after being subjected to normal harvesting and packing procedures. Its resistance to handling during harvest and packing and its long shelf life without alteration after harvest easily permit 3 weeks to 4 weeks-shipping at 2 degrees Celsius.

Resistance to insects and disease: No particular susceptibilities were noted. The present variety is not very sensitive to powdery mildew, or conservation diseases and decay due to its thick and strong skin. Fruits seem not sensitive to Monilia.

Although the new variety of peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of peach tree as illustrated and described, characterized by fruit of very long shelf life without alteration after harvesting, and with semi-sweet yellow flesh of high eating quality and an attractive skin, with a very high percentage of red blush.

* * * * *

UNITED STATES PATENT AND TRADEMARK OFFICE

CERTIFICATE OF CORRECTION

PATENT NO. : PP19,178 P3
APPLICATION NO. : 11/783784
DATED : September 2, 2008
INVENTOR(S) : Arsene Maillard et al.

It is certified that error appears in the above-identified patent and that said Letters Patent is hereby corrected as shown below:

On the title page, Item (30):
Change

"Apr. 24, 2006 (FR) .....2006-0997"

to be

-- Apr. 24, 2006 (QZ) .....2006-0997 --

Signed and Sealed this
Eighteenth Day of February, 2014

Michelle K. Lee

Michelle K. Lee
*Deputy Director of the United States Patent and Trademark Office*